United States Patent [19]

Walker

[11] 4,193,139
[45] Mar. 18, 1980

[54] PROSTHETIC FINGER JOINT

[75] Inventor: Peter S. Walker, Ridgewood, N.J.

[73] Assignee: Codman & Shurtleff, Inc., Randolph, Mass.

[21] Appl. No.: 884,786

[22] Filed: Mar. 8, 1978

[51] Int. Cl.² ............................................... A61F 1/24
[52] U.S. Cl. .................................... 3/1.91; 128/92 C
[58] Field of Search ................................. 3/1.9–1.913; 128/92 C

[56] References Cited

U.S. PATENT DOCUMENTS

| | | | |
|---|---|---|---|
| 3,765,033 | 10/1973 | Goldberg et al. | 3/1.911 |
| 3,772,709 | 11/1973 | Swanson | 3/1.91 |
| 3,899,796 | 8/1975 | Bahler | 3/1.91 |
| 4,085,466 | 4/1978 | Goodfellow et al. | 3/1.91 |

FOREIGN PATENT DOCUMENTS

| | | | |
|---|---|---|---|
| 2114287 | 9/1972 | Fed. Rep. of Germany | 3/1.911 |
| 2122390 | 1/1973 | Fed. Rep. of Germany | 3/1.911 |
| 2445758 | 4/1975 | Fed. Rep. of Germany | 3/1.91 |

*Primary Examiner*—Ronald L. Frinks

[57] ABSTRACT

A prosthetic joint is comprised of three basic components. A first component is adapted to be associated with a first bone and has an arcuate bearing surface at one end thereof. The first component is constructed such that it may pivot on its bearing surface. A second component is adapted to be associated with a second bone adjacent to the first bone. The second component has a terminal portion at one end facing toward the bearing surface of the first component and has rigid walls defining an open-ended socket. The walls of the second component are connected to the first component in a manner to allow pivoting of the first component with respect to the second component. A third component has an arcuate bearing surface mating with the arcuate bearing surface on the first component. The third component is located in the open-ended socket with its walls embracing the same so that the mating bearing surfaces cooperate to carry the loading forces of the joint in use.

17 Claims, 4 Drawing Figures

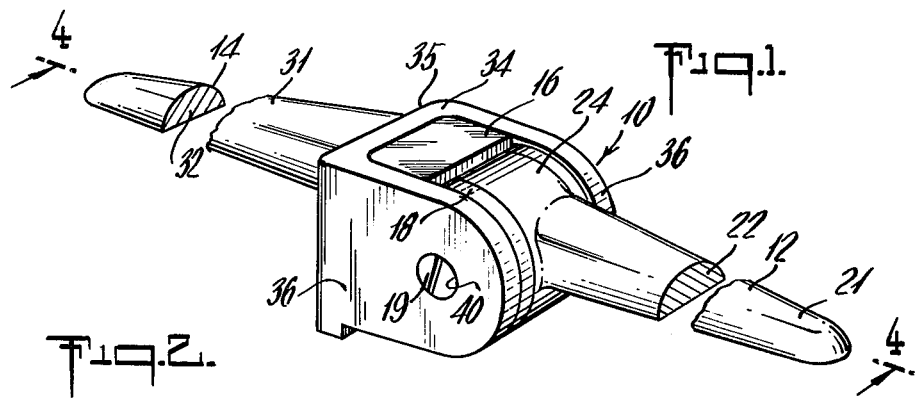
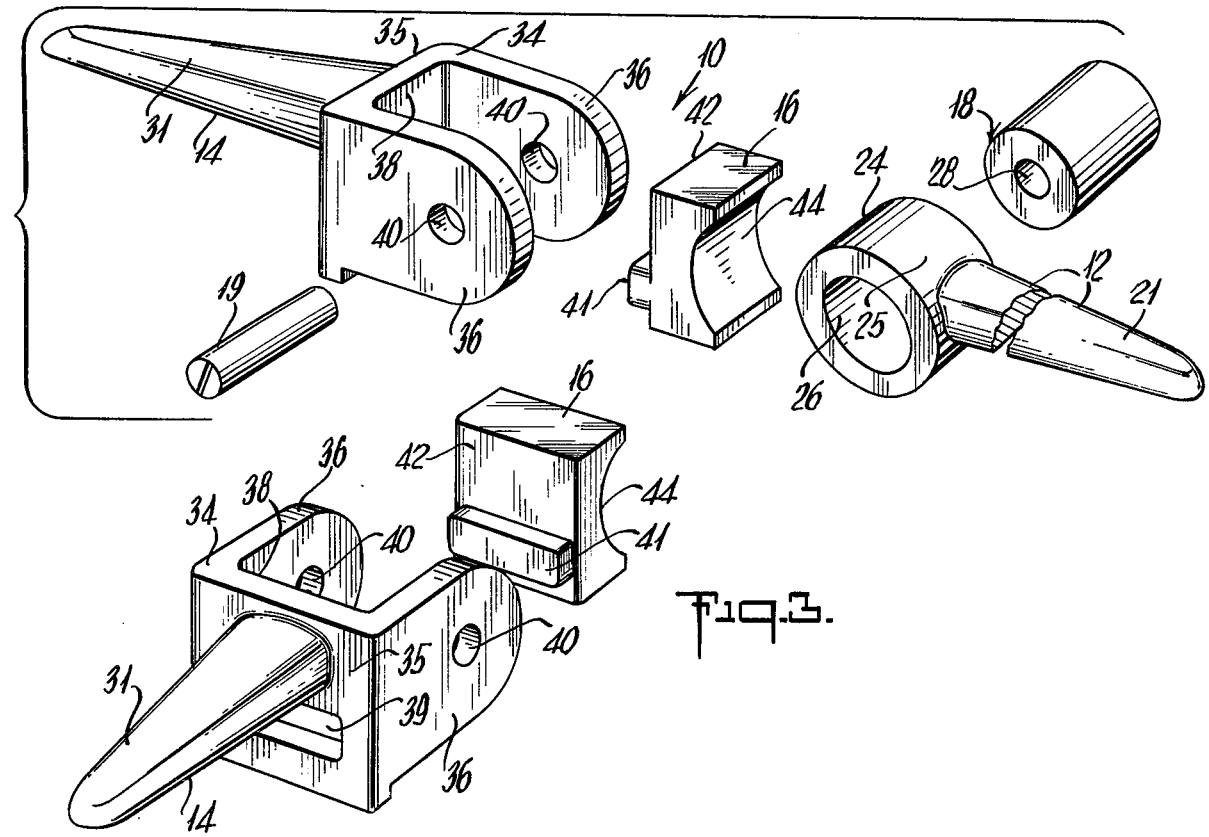
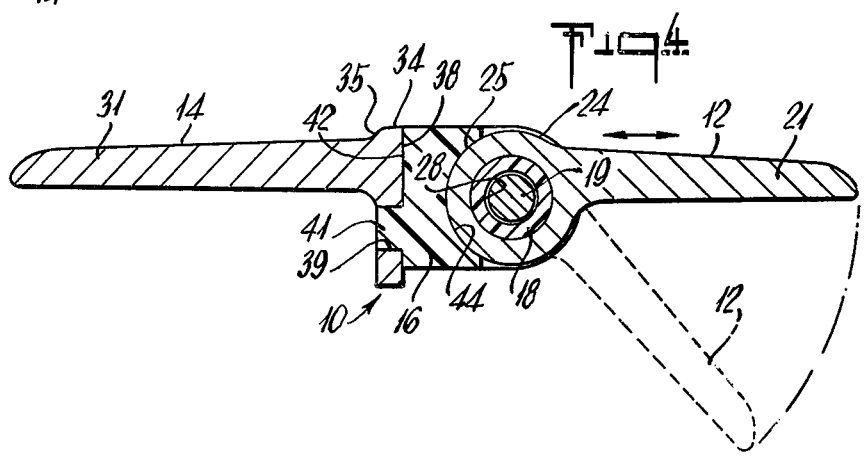

PROSTHETIC FINGER JOINT

BACKGROUND OF THE INVENTION

This invention relates generally to a prosthetic joint and, more particularly, concerns a hinge type prosthetic joint for replacement of a natural joint in the human body especially when relative movement of the components of the joint is generally in one plane.

Replacement of defective, deteriorated or otherwise nonfunctioning natural joints by mechanical prosthetic devices has become more prevalent due to the recent advances in the specific designs of the prostheses and the surgical techniques to implant them in the patient. Individuals who have joints with limited or no movement, accompanied by pain and discomfort, such as with severe rheumatoid arthritis may undergo a surgical treatment to replace the affected joint, including treatments such as resection arthroplasty. In resection arthroplasty, the articulative portions of the natural joint are removed, and the bones are prepared to receive the prosthesis as a substitute for that particular joint. In addition to relief of pain and discomfort, it is expected that the prosthesis will allow the individual to regain use of the affected joint in a way which resembles, as close as possible, the use and function of the original natural joint. Factors such as relative movement, stability, strength compatibility in the human body, durability and the like must be taken into consideration in the design of the prosthesis. The goal of designing the prosthesis is to achieve a mechanical joint which, although a substitute, functions substantially equivalently to the natural joint which it replaces.

In a number of joints in the human body, the bone components which form the same have movement with respect to each other generally in one plane, i.e., one bone swings in a rotative movement with respect to the other in a hinging effect. This type of movement is found, for example, in the finger joints, such as the proximal interphalangeal (PIP) joint. Although there may be some rocking movement or action in the natural PIP joint, the rotative movement of the bones forming the joint is generally in one plane. Many prostheses which are designed to replace, for example, the PIP joint or similar type joint, include an axle which is used to pin together the components of the joint and thereby allow hinge-type rotation of the components. In these hinge-type prostheses, not only is the axle or pin relied upon to provide a pivot point, but also to act as a bearing surface to carry the loading forces of the joint in use. Such a prosthetic joint wherein an axle is employed for hinging purposes and also as a load bearing member is typified in U.S. Pat. No. 3,879,766. Inasmuch as the axle is generally a slender member, it is undesirable to place reliance on the axle to carry unexpectedly large loading forces or to possess durability during the period of time the prosthesis is implanted. In this regard, hinge-type prostheses which include an axle or pin to hold the components together, and which relay upon the axle as a bearing surface to dissipate the loading forces of the joint, may be somewhat weak from the standpoint of joint strength. It can be seen that the search for mechanical replacements for particular natural joints remain viable insofar as improvements in the particular designs are still sought.

SUMMARY OF THE INVENTION

The prosthetic joint of the present invention comprises three basic components. A first component is adapted to be associated with the first bone, and has an arcuate bearing surface at one end thereof. This first component includes means for allowing the same to pivot on the bearing surface. A second component is adapted to be associated with a second bone adjacent to the first bone. This second component has a terminal portion at one end facing toward the bearing surface of the first component. The terminal portion has rigid wall means defining an open-ended socket, with the wall means including means therewith for cooperating with the pivot allowing means with the first component to allow pivoting of the first component with respect to the second component. A third component has an arcuate bearing surface mating with the arcuate bearing surface on the first component. The third component is located in the open-ended socket of the second component so that the wall means thereof embraces the same so that the mating bearing surfaces cooperate to carry the loading forces of the joint.

In the preferred embodiment of the prosthetic joint of this invention, the first and second components are stemmed components for insertion in the intramedullary canals of bones, respectively prepared to receive the same. The first stemmed component has a substantially cylindrical member at one end, wherein the peripheral surface thereof defines a convex arcuate bearing surface. The cylindrical member has a passage extending transversely therethrough. A bushing is inserted in tight fit in the passage and has a hole extending therethrough concentrically with the convex bearing surface. This hole is adapted to receive axle pinning means so that the first stemmed component may pivot about the hole. On the second stemmed component the wall means includes a pair of rigid walls spaced apart from one another to define the openended socket. Each of the walls has an opening therein also adapted to receive the axle pinning means, the openings being in alignment with and astride of the hole in the bushing. A pinning axle interconnects the first and second stemmed components, the axle extending through the hole in the bushing and into each of the openings in the rigid walls so that the first component may pivot with respect to the second component. This axle is sized to leave sufficient clearance in the hole so that the bearing surfaces of the components mate with each other during loading of the joint in use thereby cooperating to carry the forces experienced under that loading. In this embodiment, the third component has a concave bearing surface to mate with the convex bearing surface.

In accordance with this invention, the structure of this prosthetic joint is notably different from previously known prosthetic joints, particularly of the hinge type. In this respect, the prosthetic joint of the present invention, although including an axle or pinning means in order to facilitate pivoting of the components, does not rely upon the axle as a load dissipating bearing surface as previous devices have so relied. Instead, the instant prosthetic joint includes mating arcuate bearing surfaces of two components cooperating to carry the loading forces of the joint in use; the axle acts to interconnect the two components, to maintain their connection after implantation, and to provide a pivot point about which one component may rotate with respect to the other.

A significant advantage of the present invention lies in the strength and durability imparted to this new design, in addition to a certain amount of laxity provided to the joint. This laxity prevents the joint from being too rigid and from developing excessive stresses during loading of the joint. Joint stability also results from the cooperative arrangement of the components of this present invention.

BRIEF DESCRIPTION OF THE DRAWINGS

FIG. 1 is a perspective view illustrating the preferred embodiment of the prosthetic joint of the present invention;

FIG. 2 is an exploded view of the components of the prosthetic joint of FIG. 1;

FIG. 3 is a perspective view illustrating the locking arrangement of the second stemmed component and the bearing pad; and FIG. 4 is a cross-sectional view taken along lines 4-4 of FIG. 1.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and it is not intended to limit the invention to the embodiment illustrated. The scope of the invention will be pointed out in the appended claims.

Adverting to the drawings, particularly FIGS. 1-3, there is illustrated a prosthetic joint 10 embodying the features of the present invention. Prosthetic joint 10 is comprised of the following elements: a first stemmed component 12; a second stemmed component 14; a bearing pad 16; a bushing 18; and an axle 19.

Turning to first stemmed component 12, it includes an elongated, slender stem 21, preferably having a somewhat roughened finish in order to provide a better grip for the bone cement. This stem is to be inserted into the intramedullary canal of a bone, such as the middle phalangeal bone of the finger, which has been surgically prepared to receive the stem. Depending upon the particular natural joint which prosthetic joint 10 is replacing, the length, cross-sectional shape and contour of stem 21 may vary; in addition, characteristics of bones of different individuals into which the prosthesis is introduced dictate a variety of stem differences. When intended to be inserted in the middle phalangeal bone, stem 21 is preferentially straight and has a cross-sectional shape in the form of a hemicircle 22 to conform to the normal bone canal shape and to prevent rotation when fixed in place. At one end of stem 21 is a substantially cylindrical member 24 wherein its peripheral surface defines a convex arcuate bearing surface 25. Arcuate bearing surface 25 is polished smooth, so as to facilitate the pivoting motion of the first component of the joint in use, and also to reduce unnecessary friction in the movement of the joint, thus reducing wear of pad 16. Extending transversely through cylindrical member 24 is a tubular passage 26. In the embodiment being described, passage 26 is adapted to receive bushing 18, which is inserted in the passage in tight fit so as to be securely maintained therein. Bushing 18 is generally a hollow cylinder with a hole 28 extending therethrough. When the bushing is inserted in passage 26, hole 28 is oriented so as to be concentric with convex bearing surface 25 so that when first component 12 pivots, arcuate surface 25 becomes the main load bearing surface. To facilitate this pivoting, hole 28 is adapted to receive axle 19, which also serves to pin the components together.

Bushing 18 is preferably incorporated in the structure of this embodiment so as to provide more durability, longer wear and less friction to the pivoting components. However, it is understood that bushing 18 may be eliminated, whereupon passage 26 in cylindrical member 24 is adapted to receive axle 19. In that case, passage 26 is oriented concentrically with arcuate bearing surface 25 to assure that bearing surface 25 is the load bearing surface during pivoting of first component 12.

Referring now to second stemmed component 14, the same includes an elongated, slender stem 31 which is similar in many respects to stem 21 of the first component; stem 31 is to be inserted in the intramedullary canal of a second bone adjacent the first bone so that an articulative joint may be formed. This second bone, for example, may be the proximal phalangeal bone for forming one member of the proximal interphalangeal (PIP) joint, and it is also prepared during surgery to receive stem 31 of the second component. While stem 31 may have variations in its length, cross-sectional shape and contour, when used as a proximal phalangeal component, the stem is preferentially straight and has a cross-sectional shape in the form of a hemi-circle 32 to conform to the normal bone canal shape and to prevent rotation when fixed in place.

At one end of stem 31 is a terminal portion 34 which has a substantially flat backsurface 35 which abuts against stem 31 and is the surface which rests upon the bone to provide support and location. In the formed joint, terminal portion 34 faces toward convex bearing surface 25, and has a pair of rigid walls 36 extending therefrom. Walls 36 are spaced apart from each other and collectively define an open-ended socket therebetween. For maximum strength, rigid walls 36 are preferably integrally formed in the terminal portion such as a unitary U-shape structure. Strength is significant in these walls since they anchor axle 19 in the interconnection of the components. The peripheral edges of the rigid walls may be rounded, as shown, squared or otherwise shaped, as desired. The surface 38 of terminal portion of 34 opposite stem 31 between rigid walls 36 is preferably a flat surface against which bearing pad 16 locates in the formed joint. A recess 39 is formed in terminal portion 34, and in this instance, extends from flat surface 38 to backsurface 35, completely therethrough. Recess 39 is essentially an elongated slot which is adapted to receive protruding ridge 41 on bearing pad 16, as hereinafter discussed. A substantially circular opening 40 is located in each wall 36, each being positioned respectively therein to face each other, and are thus adapted to receive axle 19 for pinning purposes. In the formed joint, openings 40 are aligned with and astride of hole 28 in bushing 18 so that the components may be readily interconnected.

Bearing pad 16 is located between rigid walls 36, preferbly in a tight, snug fit. Rear wall 42 of bearing pad 16 is substantially flat and locates against flat wall 38 in the terminal portion of the second component. Protruding from rear wall 42 is a ridge 41 which is received in recess 39. Thus, not only is bearing pad 16 tightly located in the openended socket, but the ridge and recess combination serve to lock the bearing pad and the second component securely together. It can be appreciated that various combinations of protruding ridges, recesses and the like can be adapted to perform this locking function.

The surface of bearing pad 16 is opposite the ridged surface, is concavely curved to serve as an arcuate bearing surface 44. Arcuate bearing surface 44 has a radius of curvature to substantially mate with convex arcuate bearing surface 25 of the first component. In the formed joint, concave arcuate bearing surface 44 and convex arcuate bearing surface 25 mate with each other and cooperate to serve as the main load bearing surfaces to carry the forces experienced by the joint in use. In addition, the mating arcuate surfaces allow smooth and ready pivoting of first component 12 with respect to second component 14, so that, irrespective of orientation of those two components, the loading forces will still be carried on the arcuate bearing surfaces.

Axle 19 is employed to interconnect first component 12 and second component 14. Axle 19 is a substantially smooth, cylindrically shaped rod which extends through hole 28 in bushing 18 and terminates in each opening 40 in rigid walls 36. By crimping the ends of axle 19 in hole 40, the axle is secured in place, and first component 12 is free to pivot thereabout.

In order to assure that arcuate bearing surfaces 25 and 44, and not axle 19, carry the loading forces of the joint in use, axle 19 is sized to leave sufficient clearance in hole 28 so that the respective bearing surfaces may mate with each other. This size relationship and the mating of the bearing surfaces is more clearly illustrated in FIG. 4. It can be seen that the clearance between axle 19 and the wall of the bushing surrounding hole 28 provides a certain degree of laxity to first component 12. In this regard, first component 12 may move slightly inwards and outwards, thereby reducing the rigidity of the joint and any concomitant stress forces. When the joint is loaded, however, such as in pinching, gripping, or the like, convex bearing surface 25 on the first stem component mates with concave bearing surface 44 on the bearing pad to carry and absorb the forces that are transmitted along the loaded joint. Axle 19 remains substantially out of contact with the wall of bushing 18 when the joint is loaded; if the axle should be in contact with the bushing in the loaded position, it assists in carrying the loading forces, but only in a secondary fashion. Of course, when first component 12 pivots with respect to second component 14, as illustrated in FIG. 4, the respective arcuate bearing surfaces continue to serve as the main load bearing surfaces. The range of pivotal rotation of the first component with respect to the second component varies according to the specific natural joint being replaced by the prosthetic joint.

Both the first and second stemmed components, and the pinning axle are preferably made of metals such as colbaltchrome alloy, medical grade stainless steel, and medical grade titanium alloy, but other metallic or rigid plastic materials, bio-compatible to the human body may also be used. Metal components are preferred because they provide the strength to the joint and wear well over extended periods of time. Both the bearing pad and the bushing are preferably made of a bio-compatible high wear, rigid plastic material, such as high molecular weight polyethylene, for example, although other similar materials may be used. The rigid plastic material provides minimal friction to the surfaces on which relative movement or rotation is to be experienced, in addition to being light-weight with good wear qualities.

Thus, there has been provided a prosthetic joint for implantation in the human body as a substitute for a natural joint wherein the loading forces experienced by the prosthetic joint in use are carried on mating load bearing surfaces and not on the axle pinning means which interconnects the components of the joints.

What is claimed is:

1. A prosthetic finger joint comprising: a first stemmed component having a stem for insertion in the intramedullary canal of a first bone of the finger, said first component having a convex arcuate bearing surface at one end thereof and having tubular passage means extending transversely therethrough for receiving pinning means, so that said first component may pivot about said pinning means, said passage means and said convex bearing surface being concentric to each other; a second stem component having a stem for insertion in the intramedullary canal of a second bone of the finger adjacent to said first bone, said second component having a terminal portion at one end facing toward said convex bearing surface, said terminal portion having a pair of rigid walls spaced apart from one another and collectively defining therebetween an open-ended socket, each of said walls having an opening therein adapted to receive pinning means, said openings being in alignment with and astride of said passage means of said first component; a bearing pad having a concave arcuate bearing surface mating with said convex arcuate bearing surface on said first component, said pad fixedly located between said rigid walls which embrace the same so that there is no relative movement between said pad and second second component; and pinning means interconnecting said first and second components, said pinning means extending through said passage means and into each of said openings in said rigid walls, whereby the first component may pivot with respect to the second component, said pinning means being sized to leave sufficient clearance in said passage means so that said bearing surfaces mate with each other during loading of said joint in use thereby cooperating to carry the forces experienced under said loading.

2. A prosthetic joint as defined in claim 1 wherein the stem of one of said stemmed components has a cross-sectional shape in the form of a hemi-circle.

3. A prosthetic joint as defined in claim 1 which further includes a ridge on said pad and a recess in said terminal portion of said second component adapted to receive said ridge to thereby lock said second component and said pad in position.

4. A prosthetic joint as defined in claim 1 wherein said convex arcuate bearing surface is the peripheral surface of a substantially cylindrical member, said cylindrical member having said transverse passage means extending therethrough.

5. A prosthetic joint as defined in claim 1 which further includes a bushing in tight fit in said passage means of said first component, said bushing having a hole extending therethrough concentrically to said convex bearing surface, said hole adapted to receive said pinning means for interconnecting said first and second components.

6. A prosthetic joint as defined in claim 5 wherein said bushing is made of rigid plastic.

7. A prosthetic joint as defined in claim 1 wherein said pinning means is a cylindrically shaped axle, the ends of which are securely fixed in said openings in said walls of said second component.

8. A prosthetic joint as defined in claim 1 wherein said first and said second components and said pinning means are metal, and said pad is rigid plastic, all of said materials being bio-compatible.

9. A prosthetic joint as defined in claim 1 wherein the stem of each of said stemmed components has a cross-sectional shape in the form of a hemi-circle.

10. A prosthetic finger joint comprising: a first component adapted to be associated with a first bone of the finger, said first component having an arcuate bearing surface at one end thereof, said first component including means for allowing said first component to pivot on said bearing surface; a second component adapted to be associated with a second bone adjacent to said first bone, said second component having a terminal portion at one end facing toward said arcuate bearing surface, said terminal portion having rigid wall means defining an open-ended socket, said wall means including means therewith for cooperating with said pivot allowing means of said first component to allow pivoting of said first component with respect to said second component; and a third component having an arcuate bearing surface mating with said arcuate bearing surface on said first component, said third component fixedly located in said open-ended socket so that said wall means embraces the same and so that there is no relative movement between said second and third components, said mating bearing surfaces cooperating to carry the loading forces of said finger joint in use.

11. A prosthetic joint as defined in claim 10 wherein said arcuate bearing surface on said first component is convexly curved, and wherein said mating arcuate bearing surface on said bearing pad is concavely curved.

12. A prosthetic joint as defined in claim 9 wherein said pivot allowing means of said first component is a passage therethrough, said passage being substantially circular in cross-section and concentric to said convex bearing surface.

13. A prosthetic joint as defined in claim 12 wherein said pivot cooperating means of said second component includes two openings in said wall means of said open-ended socket, said openings facing each other and aligned to be astride of said passage in said first component.

14. A prosthetic joint as defined in claim 13 which further includes an axle extending through said passage and into each of said openings in said wall means, so that said first component may pivot thereabout with respect to said second component.

15. A prosthetic joint as defined in claim 11 wherein said pivot allowing means is a bushing inserted in said first component, said bushing having a hole extending therethrough concentric to said convex bearing surface, said hole adapted to receive an axle for interconnecting said first and second components and for cooperating to allow pivoting of said first component with respect to said second component.

16. A prosthetic finger joint comprising: a first stemmed component having a stem for insertion in the intramedullary canal of a first bone of the finger, said first component having a substantially cylindrical member at one end wherein the peripheral surface thereof defines a convex arcuate bearing surface, said cylindrical member having a passage extending transversely therethrough; a bushing in tight fit in said passing having a hole extending therethrough concentrically to said convex bearing surface, said hole adapted to receive axle pinning means so that said first stemmed component may pivot about said pinning means; a second stemmed component having a stem for insertion in the intramedullary canal of a second bone of the finger adjacent to said first bone, said second stemmed component having a terminal portion at one end facing toward said convex bearing surface, said terminal portion having a pair of rigid walls spaced apart from one another and collectively defining therebetween an open-ended socket, each of said wall having an opening therein adapted to receive axle pinning means, said openings being in alignment with and astride of said hole in said bushing, and said terminal portion having a recess therein; a bearing pad having a concave arcuate bearing surface mating with said convex arcuate bearing surface on said first stemmed component, said pad located between said rigid walls which embrace the same, said pad including a ridge thereon adapted to fit into said recess in said second stemmed component to provide locking between said pad and said second stemmed component so that there is no relative movement between said pad and second component; and a pinning axle interconnecting said first and said second stemmed components, said axle extending through said hole in said bushing and into each of said openings in said rigid walls whereby said first stemmed component may pivot with respect to said second stemmed component, said axle being sized to leave sufficient clearance in said hole so that said bearing surfaces mate with each other during loading of said joint in use thereby cooperating to carry the forces experienced under said loading.

17. A prosthetic joint as defined in claim 16 wherein said first and said second stemmed components and said axle are metal, and said bushing and said bearing pad are rigid plastic, all of said materials being bio-compatible.

* * * * *

UNITED STATES PATENT AND TRADEMARK OFFICE
CERTIFICATE OF CORRECTION

PATENT NO. : 4,193,139
DATED : March 18, 1980
INVENTOR(S) : Peter Stanley Walker It is certified that error appears in the above–identified patent and that said Letters Patent are hereby corrected as shown below:

At Column 6, line 33, Claim 1: "second second" should be -- said second --
At Column 7, line 34, Claim 12: "as defined in claim 9" should be -- as defined in claim 11 --
At Column 8, line 13, Claim 16: "said passing" should be -- said passage --
At Column 8, line 26, Claim 16: "wall" should be -- walls --

Signed and Sealed this

Twenty-eighth Day of October 1980

[SEAL]

Attest:

SIDNEY A. DIAMOND

Attesting Officer

Commissioner of Patents and Trademarks